United States Patent [19]

Burger et al.

[11] Patent Number: 4,904,581
[45] Date of Patent: Feb. 27, 1990

[54] METHOD OF DETECTING AIDS VIRUS INFECTION

[75] Inventors: Denis R. Burger; Andrew S. Goldstein, both of Portland, Oreg.

[73] Assignee: Epitope, Inc., Beaverton, Oreg.

[21] Appl. No.: 877,609

[22] Filed: Jun. 23, 1986

Related U.S. Application Data

[63] Continuation-in-part of Ser. No. 860,169, May 6, 1986.

[51] Int. Cl.[4] .................. G01N 33/569; G01N 33/577
[52] U.S. Cl. .......................................... 435/5; 424/3; 424/7.1; 435/7; 435/29; 435/32; 435/70.21; 424/240.27; 435/172.2; 530/387; 530/808; 530/809; 935/110
[58] Field of Search ............... 435/5, 7, 29, 32, 68, 435/240.27; 424/3, 7.1; 530/387; 935/99–110

[56] References Cited

U.S. PATENT DOCUMENTS 4,629,783 12/1986 Cosand ............................. 530/324

FOREIGN PATENT DOCUMENTS 0136798 4/1985 European Pat. Off. ............... 435/5

OTHER PUBLICATIONS

McDougal et al., "Immunoassay for the Detection and Quantitation of Infectious Human Retrovirus, Lymphadenopathy-Associated Virus (LAV)", Journal of Immunological Methods, 76(1985): 171–183.
Gallo et al., "Isolation of Human T-Cell Leukemia Virus in Acquired Immune Deficiency Syndrome (AIDS)", Science, 220(1983): 865–867.
Robert-Guroff et al., "A Monoclonal Antibody Specific for a 52,000-Molecular-Weight Human T-Cell Leukemia Virus-Associated Glycoprotein Expressed by Infected Cells", Journal of Virology, 53(1985): 214–220.
Sarin et al., Biochemical Pharmacology, vol. 34, No. 22, pp. 4075–4079, 1985, "Inhibition of HTLV-III/LAV Replication by Foscarnet".
Mary E. Haper et al., "Detection of Lymphocytes Expressing Human T-Lymphotropic Virus Type III in Lymph Nodes and Peripheral Blood from Infected Individuals by in situ Hybridization", Proc. Natl. Acad. Science, U.S.A., vol. 83, pp. 772–776, Feb. 1986.
Hoxie et al., "Persistent Noncytopathic Infection of Normal Human T Lymphocytes with AIDS-Associated Retrovirus", Science, 229:1400–1402 (27 Sep. 1985).
Sarngadharan et al., "Immunological Properties of HTLV-III Antigens Recognized by Sera of Patients with AIDS and AIDS-related Complex and of Asymptomatic Carriers of HTLV-III Infection", Cancer Research 45: 4574s–4577s (Sep. 1985).
Barre-Sinoussi et al., "Analysis and Immunological Properties of Lymphadenopathy Associated Virus (LAV) Structural Proteins" from: International Symposium: Retroviruses and Human Pathology, Humana Press, Clifton, N.J., (1985), 343–351.
Fauci, "Immunopathogenesis of the Acquired Immune Deficiency Syncrome" from: Vaccines 86: New Approaches to Immunization, Cold Spring Harbor Laboratory, New York (1986), 323–325.
Montagnier et al., "Identification and Antigenicity of the Major Envelope Glycoprotein of Lyphadenopathy-Associated Virus" Virology 144: 283–289 (1985).
Sayers et al., "HLA Antibodies as a Cause of False Positive Reactions in Screening Enzyme Immunoassays for Antibodies to Human T-Lymphotropic Virus Type III" Transfusion 26: 113–115 (1986).
McDougal et al., "Cellular Tropism of the Human Retrovirus HTLV-III/LAV: I. Role of the T Cell Activation and Expression of the T4 Antigen", J. Immunol., 135: 3151–3162 (Nov. 1985).
McDougal et al., "Binding of HTLV-III/LAV to T4+ Cells by a Complex of the 110K Viral Protein and the T4 Molecule", Science 231: 382–385 (24 Jan. 1986).
Auffray et al., "Speculations on Sequence Homologies Between the Fibronectin Cell-Attachment Site, Major Histocompatability Antigens, and a Putative AIDS Virus Polypeptide", Human Immunol. 15: 381–390 (1986).
Sandstrom et al., "Detection of Human Anti-HTLV-III Antibodies by Indirect Immunofluorescence Using Fixed Cells" Transfusion 25: 308–312 (1985).

Primary Examiner—Christine M. Nucker
Attorney, Agent, or Firm—Iver P. Cooper

[57] ABSTRACT

A method is disclosed for detecting the presence of HTLV III infected cells in a medium. The method comprises contacting the medium with monoclonal antibodies against an antigen produced as a result of the infection and detecting the binding of the antibodies to the antigen. The antigen may be a gene product of the HTLV III virus or may be bound to such gene product. On the other hand the antigen may not be a viral gene product but may be produced as a result of the infection and may further be bound to a lymphocyte. The medium may be a human body fluid or a culture medium. A particular embodiment of the present method involves a method for determining the presence of a AIDS virus in a person. The method comprises combining a sample of a body fluid from the person with a monoclonal antibody that binds to an antigen produced as a result of the infection and detecting the binding of the monoclonal antibody to the antigen. The presence of the binding indicates the presence of a AIDS virus infection. Also disclosed are novel monoclonal antibodies, noval compositions of matter, and novel diagnostic kits.

46 Claims, No Drawings

METHOD OF DETECTING AIDS VIRUS INFECTION

This is a continuation-in-part of Ser. No. 860,169, filed May 6, 1986.

BACKGROUND OF THE INVENTION

1. Field of the Invention

The disease called Acquired Immune Deficiency Syndrome (AIDS) has been recognized only recently but has created an alarming situation in many parts of the world. The number of diagnosed cases per year has escalated rapidly and a large number of deaths has resulted. Until recently, the disease apparently has been prevalent primarily in homosexual men with multiple sexual partners, intravenous drug users, hemophiliacs, blood transfusion recipients, and close heterosexual contacts of members of the above group. Despite the mounting concern with regard to AIDS, the original and cure of the disease have alluded the medical and scientific community although a great deal of research has already been carried out with respect to the disease.

A major advance and understanding of the basis of AIDS has been the isolation of a novel class of retrovirus from patients suffering from AIDS or AIDS-related complex (ARC). This group of viruses is variously called lymphadenopathy virus (LAV) as referred to by S. Wain Hobson, et al., *Cell*, 40, 9-17 (1978), human T lymphotropic virus III (HTLV-III) as described by L. Ratner, et al., *Nature*, 313, 277-84 (1985) and AIDS-associated retrovirus (ARV) as disclosed by R. Sanchez Pescador, et al., *Science*, 227, 484-492 (1985). From a morphologic and biologic standpoint, this group of viruses is most closely related to the lentivirus family.

The primary targets of affliction of the AIDS virus in the human body are specific subpopulations of T-cells. The severe immune deficiency of these patients results from an unusually low proportion of T-cells (T4) in their lymphocyte population. As a result the availability of many T4 helper functions is reduced. One of such functions is the production of antibodies by the B-cells.

The pronounced depression of cellular immunity that occurs in patients with AIDS and the quantitative modifications of subpopulations of their T-lymphocytes suggests that T-cells or a subset of T-cells might be a preferential target for the putative infectious agent. Alternatively, these modifications may result from subsequent infections. The depressed celular immunity may result in serious opportunistic infections in AIDS patients, many of whom develop Kaposi's Sarcoma. Multiple lymphadenopathies have also been described in homosexual males and infants who may or may not develop AIDS. The lympadenopathies may correspond to an early or milder form of the disease.

There are currently three major tests for establishing the presence of serum antibody specific for HTLV-III virus. The most widely employed procedure is the ELISA screen which uses either wells or beads coated with HTLV-III viral lysate. Specific antibody from a seropositive specimen binds to the antigen coated surface, followed by an enzyme linked, anti-human antibody and appropriate chromogenic substrate.

The second antibody detection procedure, most often used as a confirmatory test for the ELISA screen, is the enzyme-linked immunoelectrotransfer blot or Western Blot technique. An HTLV-III viral lysate is resolved by SDS-Polyacrylamide Gel Electrophoresis (SDS-PAGE) into a series of bands, each defining a particular product of the viral genome. The antigen bands are then transblotted to a nitrocellulose membrane for use in a enzyme-linked immunosorbent assay procedure, similar to the ELISA screen. The principle advantage of the Western Blot is the resolution of the viral antigens into discreet bands providing greatly enhanced specificity. There are two bands elucidated by the Western Blot, either or both of which are considered diagnostic for HTLV-III specific antibody when detected by the ELISA portion of the test. The first band is the 24,000 dalton core protein. The second band is a 41,000 dalton glycoprotein which makes up a portion of the viral envelope. Equivocal results in the ELISA screen are frequently resolved by the Western Blot. Also, positive screens (especially among low risk group individuals) will often prove to be negative when reevaluated by the Western Blot.

The third antibody test is an indirect immunofluorescence assay using virus infected lymphoid cells which are reacted first with patient serum and then a fluorochrome-conjugated anti-human antibody. Fluorescence of the infected cells constitutes a positive test. The use of uninfected lymphoid cells provides a negative control which would detect antibody specific for the cells and not the virus.

The use of the ELISA screen and Western Blot confirmation tests for HTLV-III antibody has been a valuable screening tool for the elimination of contaminated blood products from the national blood supply as well as detection of infectious organ and sperm donors. However, the detection of serum antibody specific for HTLV-III virus is not a diagnosis of AIDS. Seropositivity does not prove that the patient has been exposed to live virus, is infectious, or has actively growing virus, nor does it provide any indication concerning the course of the disease. A significant percentage of seropositive hemophiliacs have failed to show the presence of virus in their blood by current techniques. Presumably, these individuals have been exposed to inactivated virus contained in the heat-treated factor VIII preparations. However, in other seropositive individuals the correlation between the presence of specific antibody and the ability to culture HTLV-III virus is strong.

The need for practical procedures for detecting the presence of antigens associated with HTLV-III viral infection in human body fluids is essential for a reliable diagnostic test for AIDS as well as for providing the means to evaluate the effect of several experimental drugs now being tested for their efficacy in treating AIDS victims.

Currently, the principle method for detecting HTLV-III virus in blood involves mixing patient lymphocytes with phytohemagglutin (PHA)-stimulated peripheral blood lymphocytes (PBLs) with the addition of fresh PHA-stimulated PBLs every three days. Supernatant samples are then tested every three days for the presence of reverse transcriptase. Cells are evaluated by electron microscopy for the presence of virus. Clearly, this method is restricted to facilities with high level, P3 containment as well as sophisticated tissue culture and analysis capabilities. Results may take several weeks and the reliability of infecting lymphocyte cultures with virus is questionable. Use of a cell line known as H9 has helped some but most of the above problems still exist.

2. Description of the Related Art

Certain diagnostic techniques for determining the presence of AIDS or AIDS antibodies are known. One such technique is a helper-suppresser cell assay performed on T-cells and T-cell subpopulations. The reversal of the helper-suppresser ratio is taken as an indication of the possible presence of AIDS virus. This assay has low specificity and sensitivity. Another technique involves a determination of the thymosin level, the elevation of the level being an indication of the presence of AIDS. This technique gives positive results only when the disease has reached an advanced stage. Furthermore, it has been reported that the technique fails to give consistently positive readings in all cases when AIDS is known to be present. The diagnosis of AIDS in mammalian subjects involving the use of immunocyto adherents (rosette inhibition) techniques is disclosed in European Patent Application 0154499. U.S. Pat. No. 4,520,113 discloses the serological detection of antibodies to HTLV-III in sera of patients with AIDS and pre-AIDS conditions. Antigens, means and method for diagnosis of lymphadenopathy and AIDS is disclosed in European Patent Application 558109. A late differentation antigen associated with the helper inducer function of human T-cells is described in *Nature* (1985) 318: 465–467. The diagnosis of AIDS or lymphadenopathic syndrome using specified T-lymphotropic retrovirus antigen is discussed in EPO 138 667 A2.

SUMMARY OF THE INVENTION

The present invention is directed to a method for detecting the presence of HTLV-III infected cells in a medium such as a body fluid or a culture medium. The method comprises contacting the medium with a monoclonal antibody against an antigen produced as a result of the infection and detecting the binding of the antibodies to the antigen. The antigen may be or HTLV-III viral gene product or it may be bound to such a product. Alternatively, the antigen may be a produced as a result of the infection and found on a lymphocyte such as a T-helper cell.

The invention further includes an immunoassay method for the detection of an AIDS virus related infection in a host. The method comprises combining a body fluid from the host with a monoclonal antibody that binds to an antigen that is present only when the AIDS virus infection is present and examining the combination for the presence of immune complexes comprising the antigen and the monoclonal antibody.

The invention also includes an antibody capable of binding to a serum antigen produced as a result of a human HTLV-III viral infection. The antigen may be on an HTLV-III viral gene product or it may be bound to an HTLV-III viral gene product. Alternatively, the antigen may be bound to a lumphocyte as a result of an HTLV-III virus infection. Hybrid continuous cell lines having the identifying characteristic of expressing the antibodies of the invention are also included.

Diagnostic kits are also provided and comprise in a packaged combination a monoclonal antibody capable of binding to an antigen produced as a result of an infection by the viral causative agent of AIDS or a labeled derivative of such antibody.

Another aspect of the invention concerns a method for the early detection of HTLV-III viral infection in cell cultures. The method comprises combining cells suspected of HTLV-III viral infection with a monoclonal antibody of the invention. Detection of binding of the antibody and the antigen indicates the presence of HTLV-III viral infection in the cell culture.

The invention also includes compositions of matter comprising a complex of a monoclonal antibody that binds to (a) an HTLV-III gene product or a derivative thereof and such (b) gene product or derivative. Another composition of matter in accordance with the present invention comprises a complex of (a) a monoclonal antibody capable of binding to a cell bound antigen other than an HTLV-III gene product and produced as a result of a HTLV-III infection and (b) such antigen.

DESCRIPTION OF THE SPECIFIC EMBODIMENTS

Before proceeding further with a description of the specific embodiments of the present invention, a number of terms will be defined.

"AIDS virus" means HTLV-III, ARV, LAV and related viruses known to cause or suspected to cause AIDS, ARC, LAD, and related disorders.

"AIDS related diseases" means a disease which is AIDS, Aids related complex (ARC), lymphadenopathy (LAD), progressive generalized lymphadenopathy (PGL), and related disorders that are known or suspected to be caused by an AIDS virus infection.

"Soluble AIDS antigen" means an antigen produced as a result of an AIDS virus infection not bound to a cell membrane and found characteristically in people that have been infected with an AIDS related virus.

"Cell-bound AIDS antigen" means an antigen bound to a cell membrane and found characteristically in people that have been infected with an AIDS related virus.

"Body fluid" means a liquid or semi-solid material obtained from the body of a mammalian subject. The liquid material may be sterile or nonsterile and usually contains cells. The liquid material may be employed without further treatment or the liquid material may be treated to remove cells, debris, and the like. Exemplary of body fluids are whole blood, lymphatic fluid, serum, plasma, saliva, semen, and cerebral spinal fluid. Body fluid may be removed from the subject, for example, by means of a syringe or needle or by natural expulsion.

"Cell" means a unicellular organism such as a bacterium and also refers to normal and transformed cells usually mammalian obtained from a body fluid. Cells may be infected or noninfected, or may be cultured or not cultured.

"Lymphocyte" means a variety of white blood corpuscles or cells which arise in the reticular tissue of the lymph glands and lymph nodes. The nucleus is single and is surrounded by protoplasm which is generally described as nongranular. There are small lymphocytes, which are about the size of a red corpuscle and large lymphocytes which are probably lymphocytes in their developing stage and are two or three times larger than the small lymphycytes and contain a larger proportion of protoplasm.

"T lymphocyte" means those lymphocytes originating in the thymus. The main function of T cells is regulation of the immune response of B cells via helper and suppressor functions. T cells do not make conventional antibodies and thus differ from antibody forming cells arising from the bone marrow which are designated as B lymphocytes.

"T-helper cell" means a T-lymphocyte which has a main function of regulating the immune response of B cells in a help capacity as opposed to a suppressor capacity.

"Viral gene product" means a product such as an antigen derived from the AIDS related virus by an RNA or DNA replication.

The present invention is directed to a method for detecting the presence of cells infected with an AIDS related virus such as HTLV-III in a medium. The method comprises contacting the medium with monoclonal antibodies against an antigen produced as a result of the infection and further detecting the binding of the antibodies to the antigen. If binding between the antigen and antibodies occurs, the presence of an AIDS related virus infection in the cells in the medium is indicated. The medium can be for example a body fluid or a culture medium. The antigen may be a soluble antigen or a cell bound antigen. Furthermore, the antigen may be a viral gene product, or bound to a viral gene product. Where the antigen is not a viral gene product it is produced as a result of the infection of cells with the AIDS related virus. The antigen may be bound to a lymphocyte such as for example a T-helper cell or to a macrophage. Usually, where the antigen is a viral gene product, the method involves detection of the binding of antibodies to the infected cells.

An antibody included within the scope of the present invention is capable of binding to a serum antigen produced as a result of an HTLV-III viral infection. The antigen is an HTLV-III viral gene product or is bound to a HTLV-III viral gene product. Alternatively, the antigen may be bound to a lymphocyte and is produced as a result of the HTLV-III infection. Usually, where the antigen is soluble it is not a viral gene product.

Monoclonal antibodies useful in the method of the invention may be produced according to the standard techniques of KÖhler and Milstein, *Nature* 265: 495–497, 1975. For example, partially purified viral lysates derived from the growth of HTLV-III in the human lymphoma, H9 cell line can be used as the immunogen. Samples of the HTLV-III antigen preparations are injected into a mouse and, after a sufficient time, the mouse is sacrificed and spleen cells obtained. The spleen cell chromosomes encoding the base sequences for the desired immunoglobulins are immortalized by fusing the spleen cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Various conventional ways exist for isolation and purification of the monoclonal antibodies from other proteins and other contaminants (see KÖhler and Milstein, supra).

One such monoclonal antibody useful in the method of the present invention is exemplified by a novel antibody expressed by the hybrid continuous cell line designated 3D8. This monoclonal antibody binds to determinants on antigens that are HTLV-III gene products bound to a cell. Lysates of AIDS infected cells are submitted to sodium dodecylsulphate-polyacrylamide one-dimensional gel electrophorresis (SDS-PAGE). Monoclonal antibody bound to nitrocellulose was developed with the SDS-PAGE gel according to Western Blot techniques. It was determined that the antibody 3D8 binds to a reverse transcriptase of 55 kilodaltons and 65 kilodatons (p55 and p65), a core protein of 24 kilodaltons (p24), a glycoprotein envelope antigen of 41 kilodaltons (gp41), and one undefined protein of 39 kilodaltons, (p39). The antigens designated p55 and p65, the core protein antigen p24, and the glycoprotein envelope antigen gp41 have been described in *Science* (1986) 231: 1289-1291. Undefined proteins p28, p39, p49 and p52 may be antigens which are bound to a cell but are not HTLV-III gene products. These antigens may be produced as a result of an AIDS viral infection and identify a cell as infected. On the other hand the p28, p49 and p52 proteins may be viral gene products that are not immunogenic in man. The p41, p55, and p65 antigens appear to be soluble antigens. Based on Western Blot observations the 3D8 antibody and the antibodies described below may recognize different determinants on the above described antigens. The 3D8 antibody is of the IgM isotype. The 3D8 antibody does not bind to normal lymphocytes, or cells from cell lines H9 or CEM.

Another monoclonal antibody useful in the method of the present invention is exemplified by a novel antibody expressed by the hybrid continuous cell line designated 3F7. A similar determination employing SDS-PAGE and Western Blot techniques indicated that antibody 3F7 binds to the p24 antigen, the p49 antigen, the p55 antigen, and the p65 antigen. The 3F7 antibody is of the IgG 1 isotype. The 3F7 antibody does not bind with high intensity to normal lymphocytes, H9 cells or CEM cells. By the term "high intensity" is meant that peaks for stained cells and non-stained cells in flow cytometry are separated.

Another monoclonal antibody useful in the method of the present invention is exemplified by a novel antibody expressed by the hybrid continuous cell line designated 3G12. By a combination SDS-PAGE and Western Blot techniques it was determined that antibody 3G12 binds to the p24 antigen and the p55 antigen. The 3G12 antibody is of the IgG 1 isotype. The 3G12 antibody does not bind with high intensity to normal lymphocytes or CEM cells.

Another monoclonal antibody useful in the method of the present invention is exemplified by a novel antibody expressed by the hybrid continuous cell line designated 2A11. Antibody 2A11 binds to the p24 antigen, the p39 antigen, and the p65 antigen. The 2A11 antibody is an IgM. The 2A11 antibody does not bind with high intensity to normal lymphocytes, H9 or CEM cells.

Another monoclonal antibody useful in the method of the present invention is exemplified by a novel antibody expressed by the hybrid continuous cell line designated 4G2. As determined by SDS-PAGE and Western Blot techniques the 4G2 antibody binds to the p24 antigen and the p55 antigen. The 4G2 antibody is of the IgM isotype. The 4G2 antibody does not bind with high intensity to normal lymphocytes, H9 or CEM cells.

Another monoclonal antibody useful in the method of the present invention is exemplified by a novel antibody expressed by the hybrid continuous cell line designated 1E2. This monoclonal antibody binds to the p55 antigen and the p49 antigen. The 1E2 antibody is of the IgM isotype. The 1E2 antibody does not bind with high intensity to normal lymphocytes or CEM cells.

Another monoclonal antibody useful in the method of the present invention is exemplified by a novel antibody expressed by the hybrid continuous cell line designated 3G8. Antibody 3G8 binds to the p24 antigen, the p39 antigen and the p41 antigen. The 3G8 antibody is an IgM isotype. The 3G8 antibody does not bind with high intensity to normal lymphocytes, H9 cells or CEM cells.

Another monoclonal antibody useful in the method of the present invention is exemplified by a novel antibody expressed by the hybrid continuous cell line designated 1C11. Antibody 1C11 bonds to the p55 antigen and p65 antigen. The 1C11 antibody is an IgM. Cell line 1C11 was obtained by re-cloning cell line 3D8. Apparently, cell line 3D8 is a mixture of two cell lines, namely, 3G8 and 1C11. When individual cells from 3D8 are isolated and grown, two cell lines, 3G8 and 1C11, are obtained. The combined Western Blot patterns for 3G8 and 1C11 are superimposable on the Western Blot pattern for 3D8.

Also included within the scope of the invention and the definition of monoclonal antibody are useful binding fragments of the monoclonal antibody such as Fab, F(ab')$_2$, Fv, and so forth. The antibody fragments are obtained by conventional techniques. For example, useful binding fragments may be prepared by peptidase digestion of the antibody using papain or pepsin.

While the above specific examples of the novel antibodies of the invention are directed to antibodies of the IgG and IgM classes from a murine source, this is not meant to be a limitation. The above antibodies and those antibodies having functional equivalency with the above antibody, whether from a murine source, other mammalian source including human, rat, or other sources, or combinations thereof are included within the scope of this invention, as well as other classes such as IgA, IgE, and the like, including isotypes within such classes and also other isotypes within the IgG and IgM classes. By the term "functional equivalency" is meant that the antibody is capable of binding to the above-described antigen and capable of competing with an antibody of the invention for binding to such antigen. That is, such antibody, when combined with a sample containing such antigen, will bind to such antigen and will block an antibody of the invention from binding to such antigen. Mammalian (e.g. human) monoclonal antibodies can be prepared by techniques described in Olsson et al. *Proc. natn. Acad. Sci. U.S.A.* (1980) 77:5429–5431; Engelman et al., "Human Hybridomas and Monoclonal Antibodies", Plenum Press, N.Y., N.Y., (1985). The fusion techniques are similar to those described above for the preparation of murine hybridomas. The following cell lines are exemplary of those which can be utilized in preparing the hybrid continuous cell lines: NS-1 (American Type Culture Collection, Rockville, Md., ATTC), SP2 (ATTC), HL-1 (Ventrex, Portland, Maine).

In carrying out a method in accordance with the present invention, a sample of a body fluid is secured from the subject and prepared as follows: For preparation of lymphocytes mononuclear cells are separated from the rest of the blood. For example peripheral blood is anticoagulated with heparin, diluted with an equal volume of phosphate buffer and subjected to density gradient centrifugation, thereby separating the mononuclear cells (primarily lymphocytes) from the rest of the blood. The cells are then washed in buffer and suspended in buffer with a small amount, e.g., 0.01–1%, preferably about 0.1%, gelatin and a small amount, e.g., 0.01–1%, preferably about 0.1%, sodium azide at $5 \times 10E6$ per ml. Alternatively, separation of the white blood cells can be achieved by whole blood hemolysis.

For preparation of serum, peripheral blood is drawn into a plain glass tube, allowed to clot and then centrifuged to separate the serum from the clot.

The amount of sample will depend on the nature of the particular assay method employed and the particular body fluid to be analyzed. The following sample amounts are provided by way of example and not limitation; those skilled in the art will be able to broadly practice the method of the present invention on the basis of the description provided herein. For serum or plasma samples the amount of sample generally will be in the range of about 0.1 ml to 5.0 ml, preferably 1.0 ml to 2.0 ml. For semen samples, the amount will generally be about 0.05 ml to 1.0 ml, preferably 0.1 to 0.5 ml.

The sample is next contacted with one of the aforementioned antibodies or a combination thereof under conditions for binding of the antibody to the antigen in the sample to form immune, i.e., antigen-antibody complexes. Depending on the nature of the assay, the antibody can be bound to a support or can be in an aqueous medium. The contact between the antibody and the sample is generally carried out in an aqueous buffered medium. The buffers which can be employed include phosphate, tris, bicarbonate, etc. The pH employed depends on the nature of the sample and the antibody, and is generally in the range of from about 5 to 8. The aqueous medium may additionally contain organic polar solvents in an amount of from about 0 to 40%. The organic polar solvents are water soluble and generally have from about 1 to 10 carbon atoms and from about 1 to 4 oxygen atoms. The antibody concentration will also depend on the nature of the assay and the volume of the sample to be tested. The amount of the antibody will generally be in the 0.5 $\mu$g to 2 $\mu$g per ml range.

After the period of contact between the sample and the antibody and depending on the nature of the assay, the combination may be treated to remove unreacted antibody. This can be accomplished by washing with an aqueous, usually buffered, medium. In general, the amount of wash solution should be sufficient to remove the unreacted antibody. The number and types of washing steps depend on whether a heterogeneous or homogeneous assay approach is employed.

Next, the presence of binding of the antibody to the antigen in the sample, which binding is indication of the presence of an AIDS-related virus infection in the subject, is observed. That is, the number of antigen-antibody (immune) complexes formed is determined. To make the determination of the presence of binding, means for producing a detectable signal in relation to the presence of antigen in the sample is incorporated into the assay system. For example, one may conjugate the antibody employed in the assay to a label which is a substance capable of producing a detectable signal in relation to the presence or absence of an AIDS-related viral infection. The label can be, for example, an enzyme, radioisotope, particle, support, chromogen, chemiluminescer, fluorescer, coenzyme, free radical, or bacteriophage. The number of labels employed for the antibody is generally determined by the requirements of the method of the present invention and the availability of sites for linking the label to the antibody. Methods for linking labels to antibodies are known in the art. See for example, U.S. Pat. Nos. 4,720,450; 4,235,869; 3,935,074; and 3,996,345.

Alternatively, one may employ a labeled specific binding partner for the antibody, which may be, for example, a labeled antibody specific for the antibody employed or labeled antigen that binds to the antibody. Where the monoclonal antibody is derived from a murine source, a labeled anti-mouse immunoglobulin specific for the antibody employed in the method may be used. Such immunoglobulins may be raised according to standard techniques by injecting a suitable host with the monoclonal antibody, waiting for an appropriate time, and harvesting the anti-mouse immunoglobulins from the blood of the injected host.

The method and antibodies of the invention may be adapted to most assays involving antigen-antibody reactions. The assays may be homogeneous or heterogeneous. In a homogeneous assay approach, the sample may be pretreated if necessary to remove unwanted materials. The immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and so forth. Exemplary of homogeneous assays are the enzyme modulated immunoassay technique (EMIT®) described in U.S. Pat. No. 3,817,837, the disclosure of which is incorporated herein by reference, and the like.

In a heterogeneous assay approach, the reagents are usually the sample, the antibody, and means for producing a detectable signal. The sample is generally placed on a support, such as a plate or a slide, and contacted with the antibody in an aqueous phase. The support is then separated from the liquid phase and either the support phase or the liquid phase is examined for a detectable signal employing means for producing such signal. Means for producing a detectable signal in heterogeneous assays includes the use of radioactive labels, fluorescers, enzymes, and so forth. Exemplary of heterogeneous immunoassays are the radioimmunoassy (RIA), immunofluorescence methods, enzyme-linked immunoassays, such as the enzyme-linked immunosorbent assay (ELISA, see U.S. Pat. Nos. 3,654,090; 3,839,153; 3,850,752; 4,016,043; and Re 29,169; the disclosures of which are incorporated herein by reference), and the like.

For a more detailed discussion of the above immunoassay techniques, see "Enzyme-Immunoassay," by Edward T. Maggio, CRC Press, Inc. Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

A particular embodiment of an assay in accordance with the present invention, by way of illustration and not limitation, involves the use of a support such as a slide or a well of a petri dish. The technique involves fixing the sample to be analyzed on the support with an appropriate fixing material such as acetone and incubating the sample on the slide with a monoclonal antibody of the invention. After washing with an appropriate buffer such as, for example, phosphate buffered saline, the support is contacted with a labeled specific binding partner for the monoclonal antibody. After incubation as desired, the slide is washed a second time with an aqueous buffer and the determination is made of the binding of the monoclonal antibody to the sample. If the label is fluorescent, the slide may be covered with a fluorescent antibody mounting fluid on a cover slip and then examined with a fluorescent microscope to determine the extent of binding. On the other hand, the label can be an enzyme conjugated to the monoclonal antibody of the invention and the extent of binding can be determined by examining the slide for the presence of enzyme activity, which may be indicated by the formation of a precipitate, a color, or the like.

Another specific embodiment of the present invention involves the use of a surface to which the monoclonal antibody of the invention is attached. The underlying structure of the surface may take different forms, have different compositions and may be a mixture of compositions or laminates or combinations thereof. The surface may assume a variety of shapes and forms and may have varied dimensions, depending on the manner of use and measurement. Illustrative surfaces may be pads, beads, discs, or strips which may be flat, concave or convex. Thickness is not critical, generally being from about 0.1 to 2 mm thick and of any convenient diameter or other dimensions. The surface typically will be supported on a rod, tube, capillary, fiber, strip, disc, plate, cuvette and the like. The surface will typically be porous and polyfunctional or capable of being polyfunctionalized so as to permit covalent binding of the monoclonal antibody of the invention as well as to permit bonding of other compounds which form a part of a means for producing a detectable signal.

A wide variety of organic and inorganic polymers, both natural and synthetic, and combinations thereof, may be employed as the material for the solid surface. Illustrative polmers include polyethylene, polypropylene, poly(4-methylbutene), polystyrene, polymethracrylate, poly(ethylene terephthalate), rayon, nylon, poly(vinyl butyrate), silicones, polyformal-dehyde, cellulose, cellulose acetate, nitrocellulose, latex, etc. Other materials which may be employed include paper, glasses, ceramics, metals, metaloids, semiconductor materials, cermits, silicates or the like. Also included are substrates that form gels, gelatins, lipopolysaccharides, silicates, agarose and polyacrylamides or polymers which form several aqueous phases such as dextrans, polyalkylene glycols (alkylene of 2 to 3 carbon atoms) or surfactants such as phospholipids.

The binding of the monoclonal antibody of the invention to the surface may be accomplished by well known techniques, commonly available in the literature. See, for example, "Immobilized Enzymes," Ichiro Chibata, Halstad Press, New York (1978) and Cuatrecasas, *J. Bio. Chem.*, 245:3059 (1970).

In carrying out the assay in accordance with this embodiment of the invention the sample is mixed with an aqueous medium and the medium is contacted with the surface containing the monoclonal antibody of the invention. Members of a signal producing system and any ancillary materials may also be included in the aqueous medium, either concurrently or added subsequently so as to provide a detectable signal associated with the surface. The means for producing the detectable signal can involve the incorporation in the medium of a labeled analyte or it may involve the use of a second monoclonal antibody having a label conjugated thereto. Separation and washing steps will be carried out as needed. The signal detected is related to the presence of a AIDS related infection. It is within the scope of the present invention to include a calibration as well as the measurement surface on the same support.

For an expanded discussion of the various general techniques discussed above with regard to conducting an assay on a surface see U.S. Pat. Nos. 4,299,916; 4,391904; 4,533,629; and 4,540,659; the disclosures of which are incorporated herein by reference in their entirety.

Another example of a technique in accordance with the method and novel antibodies of the present invention is a non-flow cytometric technique. The sample to be analyzed and a monoclonal antibody of the present invention conjugated to a label are combined and incubated under conditions that will provide for agglutination when an AIDS related virus antigen is present in the sample. Desirable incubation times are about 10 to 600 seconds, preferably about 10 to 200 seconds at mild temperatures usually about 10° to 37° C. After incubation the medium is examined to determine any change in fluorescence as a result of agglutination. To this end one may use a non-flow cytometric technique in which a small diameter beam of light produced by means of slits or preferably a laser is used to differentiate particles based on their relative size. This technique employs fluorescent pulse height analysis or correlation of fluorescence fluctuations: Briggs, et al., "Homogeneous Fluorescence Immunoassay," *Science*, 212:1266–1267 (1981) and Nicoli, et al., "Fluorescents Immunoassay Based on Long-time Correlations of Number Fluctuations," *Proc. Natl. Acad. Sci. USA*, 7 (8):4904–4908 (1980). A preferred method for determining a change of fluorescence in a non-flow-cytometric technique involves the use of a fiber optic cytometer described in U.S. Pat. No. 4,564,598, the disclosure of which is incorporated herein by reference in its entirety. Method and apparatus are disclosed for determining the presence of particles in a dispersion in relation to the detection of the presence or amount of a material of interest. An optical fiber is used to define a relatively small volume from which fluorescent light can be received and counted. The volume is related to the volume in which there is likely to be only a single particle or a few particles which result in a predetermined fluctuation. By employing a variety of techniques, which allow for changes in fluorescence fluctuations in relation to the presence of an analyte in the sample, the presence of the analyte can be determined. The fluctuations are observed over a period of time in a static mode or by sampling a plurality of volumes in the sample. A determination is then made by comparing the observed results obtained with solutions having a known amount of analyte, the amount of analyte.

Another specific embodiment of the present invention involves the use of the monoclonal antibodies of the invention in a "whole cell ELISA" test for the detection of HTLV-III expression on lymphocytes. Briefly, in a spectrophotometric procedure, peripheral blood lymphocytes are isolated by, for example, density gradient centrifugation and suspended in an aqueous protein containing, medium, for example, an aqueous medium containing fetal bovine serum, glutamine, and RPMI/640. A small sample, for instance, 50 μl, of the cell suspension can be added to wells of a 96-well microtiter plate and incubated, for example, for about 1 minute to 5 hours. After washing the cell-coated wells, a sample of an antibody of the invention is added to each well and incubated for 1 minute to 3 hours. After washing, chromogenic substrate, for example, orthophenylenediamine and hydrogen peroxide, is added to each well and incubated for 1 minute to 1 hour. Results can be read spectrophotometrically. In a microscopic procedure, buffered lymphocytes in suspension are incubated with antibody for 1 minute to 3 hours at a temperature of 0° C. to 37° C. The cells are washed and then mixed with enzyme-labeled antibody for the above antibody for 1 minute to 3 hours at 0° C. to 37° C. After washing, enzyme substrate is added and the cells are examined for the presence of a signal.

Another embodiment in accordance with the present invention involves the use of a Dot Blot technique to detect the presence of an antigen associated with an AIDS related viral infection. In such an approach a small sample, e.g., 1 μl, of patient serum is placed on a nitrocellulose strip next to a sample of normal serum. The strip is soaked in an aqueous buffered medium such as, e.g., phosphate buffered saline with gelatin, containing a monoclonal antibody of the invention, for a period of about 1 to 60 minutes, followed by addition of labeled antibody for the monoclonal antibody.

In another embodiment in accordance with the present invention a flow cytometry-based detection system for HTLV-III virus on lymphocytes is employed. Flow cytometry means analysis by fluorescence-activated cell sorter (FACS). The principle of operation of flow cytometry have been reviewed in detail. See for example Bonner et al., *Rev. Scient. Instrum.* (1972) 43:404–409; Herzenberg et al., *Proc. natn. Acad. Sci. U.S.A.* (1979) 76:1453–1455; Miller et al., *J. Immunol. Methods*, (1981) 47:13–24; Loken et al., Ibid (1982) 50:R85–R112; and Kruth, *Anal. Biochem.* (1982) 125:225–242. A single cell suspension of the sample labeled with a fluorescent antibody is passed in single file through a narrow laser beam. The emitted fluorescence is collected by an optical system at right angles to the illumination. The emitted fluorescence of each individual cell is measured and stored and determination of the presence of the antigen in question is made from the stored data.

Another aspect of the present invention involves the detection of a AIDS-related viral infection by the short term viral culture of clinical samples. The sample is cultured with H9 or CEM cells followed by detection utilizing the principles of flow cytometry, slide tests, or the like. "H9" means a T-cell lymphoma cell line. "CEM" means a-cell lymphoma cell line. By "short term" is meant 2 to 48 hours, preferably 10 to 24 hours as compared to the present method which requires 20 to 30 days.

It is also within the scope of the present invention to employ the present methods and novel monoclonal antibodies in conjunction with screening test for the detection of antibodies to the AIDS-related viral antigens in serum. For example, patient samples can be screened utilizing a known antibody detection procedure. Patients identified as positive for the presence of such antibodies can be identified accordingly. Samples taken from such patients can then be analyzed in accordance with the present invention to determine whether there is an AIDS-related viral infection present in such patient.

The invention also includes diagnostic kits for carrying out the method disclosed above. In the kit the reagents can be provided in packaged combination, in the same or separate containers so that the ratio of reagents provides for substantial optimization of a signal response to variations in analyte concentrations. In one embodiment, the diagnostic kit can comprise (a) a monoclonal antibody more specifically defined above or a combination of such antibodies and (b) a conjugate of a specific binding partner for the above monoclonal antibody and a label capable of producing a detectable signal. The reagents may also include ancillary agents such as buffering agents and protein stabilizing agents, e.g., polysaccharides and the like. The diagnostic kit may further include, where necessary, other members of the signal producing system of which system the label is a member, agents for reducing background interference in a test, control reagents, apparatus for conducting a test, and the like.

In another embodiment, the diagnostic kit can comprise a conjugate of a monoclonal antibody of the invention and a label capable of producing a detectable signal. Ancillary agents as mentioned above may also be present.

EXAMPLES

The invention is demonstrated further by the following illustrative examples.

EXAMPLE 1

Production of Monoclonal Antibodies to HTLV-III Antigens

Three month old female BALB/c and RBF/DN mice were immunized with preparations of HTLV-III antigen. The antigen preparation was a partially purified viral lysate derived from growth of HTLV-III in the human lymphoma, H9, cell line, obtained from the National Cancer Institute (NCI). Individual mice were immunized with 5-20 μg antigen on polystyrene latex particles and boosted at weekly intervals with 10 μg soluble antigen administered intraveneously (I.V.) and intraperitoneally (I.P.). Sera were collected from the mice at weekly intervals and subjected to Western Blot analysis for detection of antibody against HTLV-III viral antigens. Western Blot analysis showed the progressive development of antibodies to HTLV-III antigen over the 5 week immunization period. Mice showing reactivity to HTLV-III viral antigens were selected for fusions after 3, 4, and 5 weeks of immunization. Spleenocytes were fused to either the SP2 or HL-1 myeloma cell lines using published procedures (for HL-1, Taggart, et al., *Science*, (1983) 219:1228; for SP-2, Schulman, et al., *Nature* (1978) 276:269). Screening procedures were selected to detect antibody in the 1-10 μg/ml range. The initial screen was an ELISA procedure to detect immunoglobulin production (Table 1) followed by an ELISA screen to HTLV-III antigens. Positive wells were expanded and tested by Western Blot analysis. Positive cultures by Wester Blot analysis were cloned and characterized. Hybrid continuous cell lines 3D8, 3F7, 3G12, 2A11, 4G2, and 1E2 were produced in this manner.

Several of the monoclonal antibodies expressed by the above cell lines detect multiple bands. This could indicate expression of shared epitopes on different proteins, detection of precursor molecules of differing molecular sizes or detection of a common carbohydrate determinant on distinct proteins. Treatment of the Western Blot strips with sodium periodate prior to reaction with the monoclonal antibodies did not significantly alter the pattern of staining. This observation reduces the likelihood that carbohydrate epitopes are detected by the monoclonal antibodies. None of the anti-HTLV-III monoclonal antibodies react with normal lymphocytes or mast lymphocyte cell lines. However, three of them (1E2, 3F7 and 3G12) react with H9 cells. This suggests that the HTLV-III antigen preparation contained some H9 antigens and monoclonal antibodies to H9 proteins were produced.

EXAMPLE 2

Detection of HTLV-III Antigen by Flow Cytometry

In order to evaluate the use of some of the monoclonal antibodies of the invention in detection of HTLV-III antigen expression on lymphocytes, latex beads (2.7μ) were coated with HTLV-III antigen lysates and subjected to detection of the antigen by flow cytometry. Several of the antibodies detected the HTLV-III antigen as demonstrated by a shift in fluoresence intensity when a goat anti-mouse Ig-fluorescent second antibody reagent (TAGO, Burlingame, Calif.) was employed (Table 2). These experiments demonstrated that using flow cytometry HTLV-III antigen could be detected on large particles using the monoclonal antibodies of the invention.

EXAMPLE 3

In additional experiments, the HTLV-III antigen was captured on latex beads using one of the above monoclonal antibodies. For this approach 3D8 was adsorbed to the latex beads and the beads were washed. The washed beads were then exposed to HTLV-III viral lysate, washed a second time and then mixed with a detection antibody. For detection, 3G12 was used (IgG$_1$ isotype). After washing, a fluorescent goat antimouse IgG, gamma chain specific, second antibody was reacted and the preparation evaluated by flow cytometry. As can be seen in Table 3, this capture and detection system using these two monoclonal antibodies is an effective means of identifying HTLV-III antigen. The monoclonal antibodies wwere also employed in reciprocal fashion so that 3G12 was used to capture the antigen and 3D8 was employed to identify the captured determinants.

EXAMPLE 4

Detection of HTLV-III Antigen in the Blood of AIDS Patients

The double antibody capture technique described in Example 3 was then used to capture HTLV-III antigen from blood samples from patients with AIDS and from control patients. In a comparison study with 20 confirmed HTLV-III antibody positive samples, virus was detected in 12 samples. The samples were positive by Western Blot analysis but confirmation by direct viral culture was not carried out.

The additional experiments HTLV-III antigen was detected directly in clinical specimens by blotting the specimen onto nitrocellulose and detecting the antigen by a modified ELISA technique. In such an approach, 1 μl of patient serum is placed on a strip of nitrocellulose next to 1 μl of normal serum. The strip is then soaked in PBS-gelatin for 10 minutes followed by alkaline phosphatse conjugated goat anti-mouse antibodies in PBS-gelatin for 1 hour at room temperature. After three washes, a substrate consisting of bromochlorindole phosphate (BCIP)/nitro blue tetrazolium (NBT) is applied to the strip. Viral antigen positive serum dots produce a purple dot within 10 minutes. Normal serum dots do not show any color development. The data in Table 4 show the results of these studies. Clones 3D8 and 3G8 detected HTLV-III antigen in the majority of samples from AIDS patients and AIDS positive control sera obtained from the National Cancer Institute (NCI). Direct comparison with virus culture was not carried out.

EXAMPLE 5

Detection of HTLV-III Using a Whole Cell Technique

Using a modified whole cell ELISA technique HTLV-III antigen expression was detected on lymphocytes from patients who were confirmed positive by Western Blot analysis. In this test the cells were detected microscopically. Detection can also be made spectophotometrically. In a spectrophotometric procedure, peripheral blood lymphocytes were isolated by density gradient centrifugation and suspended in RPMI 1640 with 2 mM L-glutamine and 20% fetal bovine serum at a concentration of $2 \times 10E6$ per ml. Fifty microliters of this cell suspension were added to a flat bottom well in a 96-well microtiter plate and incubated for about 3 hours. After washing the cell coated wells, anti-HTLV-III monoclonal antibody 3D8 was added to the well and incubated 1 hour. After washing, a citrte buffered orthophenylenediamine (OPD)/hydrogen peroxide substrate was added to each well and incubated 30 minutes. Positive color reactions were read by spectrophotometer. In the microscopic procedure, lymphocytes were suspended in phosphate buffered saline with 0.1% gelatin and incubated with monoclonal antibody 3D8 for 1 hour at 4° C. The cells were then washed twice and then mixed with alkaline phosphatase conjugated goat anti-mouse IgG/IgM for 1 hour at 4° C. After washing, the cells were mixed with the substrate BCIP. HTLV-III positive cells were stained light to dark blue when viewed microscopically. The results are presented in Table 5.

EXAMPLE 6

Detection of HTLV-III Expression on Lymphocytes by Flow Cytometry

HTLV-III attacks T4 lymphocytes and proliferates in those cells. Detection of HTLV-III antigen expression on T4 cells by flow cytometry using clones 3D8, 1E2, 3G12 was carried out. In this study samples were provided by the Oregon AIDS Task Force in blind fashion. The evaluations conducted included a monoclonal antibody panel consisting of $T_1$, $T_H$, $T_S$, B and NK; a Western Blot analysis; $T_H/T_S$ ratio; and the % of cells positive in the $T_{pan}$ and $T_4$ categories to the above three anti HTLV-III monoclonals. The patient groups included overt AIDS, ARC, PGL, and Western Blot positive but symptom free individuals. Controls consisted of high risk groups and low risk sex and age matched individuals. Seventy-five patients were evaulated. The data appears in Table 6. Forty of the samples came from patients with positive Western Blot analyses for HTLV-III antibody.

Monoclonal antibodies 3D8, 1E2, and 3G12 detected expression of HTLV-III antigen on both $T_{pan}$ and $T_4$ lymphocytes. There was a general correlation between disease severity and the number of positive cells. The lowest values in the patient groups were individuals who were as yet asymptomatic. The range of responses varied from 1% to 60% positive as a percentage of the $T_4$ cells with 3D8. By comparison the high risk controls ranged by 0–3%. One control individual had a value of 7.5%. Interestingly this patient had an inverted $T_H/T_S$ ratio although at this point was by Western Blot analysis negative. 1E2 and 3G12 resulted in higher background levels but also higher percentages of HTLV-III antigen expressing cells (see Table 6).

These data indicate that HTLV-III antigen expression can be effectively detected on T cells from Western Blot positive patients even in some cases where the patients are as yet asymptomatic. This may also be a means of detecting expression of the virus before antibody formation in high risk groups. Additional control groups in these studies included patients with Herpes 1 and 2, CMV and hepatitis. Patients in these viral control groups did not express antigens detected by the above monoclonal antibodies.

EXAMPLE 7

Detection of HTLV-III Antigen Expression on H9 Cells Using Flow Cytometry

The H9 cell line is commonly used to detect HTLV-III antigen by culture and subsequent evaluation for the production of reverse transcriptase in the cells. To document that the monoclonals 3D8, 1E2 and 3G12 were actually detecting HTLV-III antigen on $T_4$ cells from patients, the following control experiment using H9 cells was conducted. H9 cells were grown with two virus containing preparations, either with a cell free HTLV-III suspension or with $T_4$ lymphocytes that were expressing HTLV-III antigen. After 48 hours of culture the H9 cells were evaluated with monoclonal antibodies of the invention and control antibodies. As can be seen in Table 7 clones 3D8, 1E2, and 3G12 detected HTLV-III antigen expression on H9 cells only when the H9 cells had been infected. Infection with either cell free HTLV-III virus or HTLV-III positive $T_4$ cells was equally effective; the isotype-control monoclonal antibody had no effect.

TABLE 1

| DETECTION OF HTLV-III ANTIGEN IN COMMERCIAL SCREENING KITS | | |
|---|---|---|
| MONOCLONAL | COMMERCIAL SCREENING KIT* | |
| ANTIBODY | DILUTION | LITTON | ENI |
| 3F7 | $10^{-2}$ | 2.0 | 2.0 |
|  | $10^{-3}$ | 1.102 | 1.430 |
|  | $10^{-4}$ | 0.43 | 0.620 |
| 3D8 | $10^{-2}$ | 2.0 | 2.0 |
|  | $10^{-3}$ | 1.712 | 1.430 |
|  | $10^{-4}$ | 1.252 | 0.821 |
| 3G12 | $10^{-2}$ | 1.862 | 2.0 |
|  | $10^{-3}$ | 0.721 | 0.928 |
|  | $10^{-4}$ | 0.210 | 0.286 |
| 2A11 | $10^{-2}$ | 0.641 | 0.589 |
|  | $10^{-3}$ | 0.112 | 0.126 |
|  | $10^{-4}$ | 0.05 | 0.06 |
| 1E2 | $10^{-2}$ | 0.761 | 0.682 |
|  | $10^{-3}$ | 0.112 | 0.153 |
|  | $10^{-4}$ | 0.05 | 0.05 |

*ELISA ABSORBANCE

TABLE 2

FLOW CYTOMETRIC MEASUREMENT OF HTLV-III COATED BEADS WITH ANTI-HTLV-III MONOCLONAL ANTIBODIES

| MONOCLONAL ANTIBODY | PERCENT BEADS STAINED |
|---|---|
| 3G8 | 60 |
| 4G2 | 18 |
| 3D8 | 82 |
| 2A11 | 77 |
| 3G12 | 73 |
| 3F7 | 75 |
| 1E2 | 80 |
| Anti-β-hCG[a] | 0.8 |
| RPMI 1640[b] | 0.8 |

[a] antibody for β-human chorionicgonadotropin
[b] standard tissue culture medium

TABLE 3

HTLV-III ANTIGEN DETECTION IN SERUM BY MONOCLONAL IgM ANTIBODY CAPTURE - MONOCLONAL IgG ANTIBODY DETECTION USING LATEX BEADS

| CAPTURE ANTIBODY ON BEAD | DETECTOR ANTIBODY | TEST SPECIMEN | % STAINED BEADS |
|---|---|---|---|
| 1E2 | 3G12 | Normal human serum (N.H.S.) | 0.3 |
| 1E2 | 3G12 | HTLV-III viral lysate[a] | 66.4 |
| 3D8 | 3G12 | N.H.S. | 0.6 |
| 3D8 | 3G12 | HTLV lysate | 43.4 |
| 3D8 | 3G12 | AIDS serum[b] | 4.9 |

[a] preparation of virus infected cells from cell culture, which cells are harvested, subjected to centrifugation, and lysed with detergent.
[b] serum from patients having clinical AIDS.

TABLE 4

DETECTION OF HTLV-III BY MONOCLONAL ANTIBODY 3D8 USING A DOT BLOT TECHNIQUE

Total samples tested - 14

| SAMPLE CLASSIFICATION | NUMBER DOT BLOT POSITIVE |
|---|---|
| Clinical AIDS | 2/4 |
| WESTERN BLOT POSITIVE | 3/5 |
| WESTERN BLOT NEGATIVE | 0/5 |

TABLE 5

DETECTION OF HTLV-III BY A MICROSCOPIC WHOLE CELL ELISA TECHNIQUE USING MONOCLONAL ANTIBODY 3D8

| SAMPLE CLASSIFICATION | PERCENT STAINED LYMPHOCYTES |
|---|---|
| AIDS | 19.0 |
| AIDS | 10.5 |
| WESTERN BLOT POSITIVE | 4.4 |
| WESTERN BLOT POSITIVE | 2.3 |
| WESTERN BLOT POSITIVE | 6.8 |
| WESTERN BLOT POSITIVE | 0.4 |
| WESTERN BLOT POSITIVE | 0.6 |

TABLE 6

| GROUP | CONTROL | WESTERN BLOT POSITIVE | AIDS | ARC/PGL | ASYM[c] |
|---|---|---|---|---|---|
| Western Blot (+/−) | − | + | + | + | + |
| 3D8/T4 X ± SE | 1.4 ± 0.3 | 9.0 ± 4.2 | 25 ± 7 | 7.3 ± 1.4 | 5.8 ± 1.1 |
| RATIO: # pos/# neg | 1/35 | 26/20 | 5/1 | 10/5 | 11/14 |
| STAT | p[a]< | 0.0001 | 0.0001 | 0.0001 | 0.0001 |
|  |  |  | p[b]< 0.05 | p< 0.05 | p< 0.05 |
| 3G12/T4 X ± SE | 8.4 ± 2.8 | 28 ± 6.1 | 44 ± 10.1 | 29 ± 4.2 | 24 ± 4.8 |
| RATIO: # pos/# neg | 1/35 | 32/14 | 5/1 | 12/3 | 16/10 |
| STAT | p< | 0.0001 | 0.0001 | 0.0001 | 0.0001 |
|  |  |  | p< | NS | p< 0.06 |
|  |  |  |  | p< | NS |

[a] Mann-Whitney U Test
[b] Fisher's Exact
[c] Asym - asymptomatic patients, i.e., those who were sero-positive for AIDS antibodies but who have no overt symptoms such as enlarged lymph nodes as found in ARC or PGL patients or infectious diseases as found in AIDS patients.

TABLE 7

DETECTION OF HTLV-III EXPRESSION ON H9 CELLS

TREATMENT OF THE H9 CELL LINE

| MONOCLONAL ANTIBODY | NONE | INFECTION WITH CELL FREE VIRUS | INFECTION WITH HTLV-III + T4 CELLS |
|---|---|---|---|
| SECOND ANTIBODY CONTROL | 6.2 | 6.4 | 3.1 |
| 3D8 | 7.5 | 18.5 | 29.7 |
| 1E2 | 14.9 | 40.8 | 41.9 |
| 3G12 | 32.2 | 82.8 | 94.0 |
| ANTI-HCG CONTROL | 3.4 | 5.6 | 4.6 |

*Percent cells positive by flow cytometry

Hybrid continuous cell lines 1E2, 3D8, and 3G12 were deposited with the American Type Culture Collection (ATCC), 12301 Parklawn Drive, Rockville, MD 20852, under the Budapest Treaty on May 19, 1986, and received ATCC accession numbers HB9100, HB9101, and HB9102, respectively. Hybrid continuous cell lines 3G8 and 1C11 were deposited with the ATCC under the Budapest Treaty on May 28, 1986, and received ATCC accession numbers HB9114 and HB9115, respectively.

The invention has been described in detail with particular reference to the above embodiments. It will be understood, however, that variations and modifications can be effected within the spirit and scope of the invention.

What is claimed is:

1. A method for detecting the presence of HTLV III infected cells, which comprises contacting a sample obtained from a mammalian subject suspected of being infected with HTLV III virus with monoclonal antibodies against an antigen produced as a result of said infection and detecting the binding of said antibodies to said antigen on said cells, the binding thereof being related to the presence of HTLV III infected cells in said sample, said antigen being capable of binding to one of the antibodies secreted by a cell line having ATCC accession numbers HB9100, HB9101, HB9102, HB9114, or HB9115.

2. The method of claim 1 wherein said antigen is produced as a result of said infection and is not a viral gene product.

3. The method of claim 2 wherein said cells are lymphocytes or macrophages.

4. The method of claim 3 wherein said lymphocyte is a T-Helper cell.

5. The method of claim 1 wherein said sample is a human body fluid.

6. The method of claim 5 wherein said body fluid is selected from the group consisting of whole blood, lymphatic fluid, serum, plasma, semen, saliva, and cerebral spinal fluid.

7. The method of claim 1 wherein said antigen is a viral gene product or bound to a viral gene product.

8. The method of claim 1 wherein said monoclonal antibodies are murine antibodies.

9. The method of claim 1 wherein said monoclonal antibodies are prepared by immunization with a lysate of HTLV-III infected H9 cell culture.

10. The method of claim 1 wherein said antigen is selected from the group of antigens characterized as molecules of approximately 24, 28, 39, 41, 55, 65, 49, and 52 kilodaltons, respectively.

11. The method of claim 1 wherein said antibody is conjugated to a label.

12. An immunoassay method for the detection of an AIDS virus related infection in a human host, which comprises:
combining a body fluid from a human host with a monoclonal antibody that binds to an antigen on infected cells that is present only when said infection is present, and
examining the combination for the presence of immune complexes comprising said antigen on said infected cells and said monoclonal antibody, the presence thereof indicating the presence of an AIDS virus infection, said antigen being capable of binding to one of the antibodies secreted by a cell line having the ATCC accession numbers HB9100, HB9101, HB9102, HB9114, or HB9115.

13. The method of claim 12 wherein said antigen is a viral gene product or is bound to a viral gene product.

14. The method of claim 12 wherein said antigen is not a viral gene product and is bound to a lymphocyte.

15. The method of claim 12 wherein said monoclonal antibody binds to an antigen on the surface of lymphocytes or of macrophages.

16. The method of claim 15 wherein said lymphocytes are T-helper cells.

17. The method of claim 12 wherein said antigen is selected from the group of antigens characterized as molecules of 24, 28, 39, 41, 55, 65, 49, and 52 kilodaltons, respectively.

18. The method of claim 12 wherein said monoclonal antibody is conjugated to a label.

19. The method of claim 12 wherein said body fluid is selected from the group consisting of whole blood, lymphatic fluid, serum, plasma, semen, saliva, and cerebral spinal fluid.

20. A method for determining the presence of an AIDS-related disease in a human host, which comprises detecting the presence of a cell-bound antigen associated with said disease in a sample of a body fluid from said human host, said antigen being capable of binding to one of the antibodies secreted by a cell line having ATCC accession numbers HB9100, HB9101, HB9102, HB9114, or HB9115.

21. The method of claim 20 wherein said antigen is bound to a T-helper lymphocyte.

22. The method of claim 20 wherein said antigen is not an AIDS-relted virus gene product.

23. The method of claim 20 wherein said antigen is detected by combining said sample in an aqueous medium with a monoclonal antibody that binds to said antigen and examining for binding of said antibody with said antigen.

24. An antibody capable of binding to an antigen produced as a result of a human HTLV-III infection, said antigen being bound to a lymphocyte, said antibody being selected from the group of antibodies secreted from hybrid continuous cell lines having ATCC accession numbers HB9101, HB9100, HB9114 and HB9102, respectively.

25. The antibody of claim 24 that is monoclonal.

26. The monoclonal antibody of claim 25 conjugated to a label.

27. The monoclonal antibody of claim 26 wherein said label is selected from the group consisting of enzymes, radioisotopes, particles, supports, chromogens, chemiluminescers, fluorescers, coenzymes, free radicals, and bacteriophages.

28. The monoclonal antibody of claim 25 wherein said lymphocyte is a T-helper cell.

29. The monoclonal antibody of claim 25 which is an antibody obtained from a hybrid continuous cell line having the identifying characteristics of HB9101.

30. The monoclonal antibody of claim 25 which is an antibody obtained from a hybrid continuous cell line having the identifying characteristics of HB9100.

31. The monoclonal antibody of claim 25 which is an antibody obtained from a hybrid continous cell line having the identifying characteristics of HB9102.

32. The monoclonal antibody of claim 25 wherein said antigen is an HTLV-III viral gene product.

33. The monoclonal antibody of claim 25 wherein said antigen is bound to an HTLV-III viral gene product.

34. The monoclonal antibody of claim 25 wherein said antigen is bound to a lymphocyte as a result of an HTLV-III viral infection.

35. A hybrid continuous cell line having the identifying characteristic of expressing the antibody of claim 24.

36. A diagnostic kit comprising in a packaged combination in separate containers
a monoclonal antibody capable of binding to an antigen produced as a result of an infection by the viral causative agent of AIDS or a labeled derivative of said antibody, said antigen being bound to a lymphocyte as a result of said infection, said antigen being capable of binding to one of the antibodies secreted by a cell line having ATCC accession numbers HB9100, HB9101, HB9102, HB9114, or HB9115, and
a member of a signal producing system.

37. The kit of claim 36 wherein said label is selected from the group consisting of enzymes, radioisotopes, particles, supports, chromogens, fluorescers, chemiluminescers, coenzymes, free radicals, and bacteriophages.

38. The kit of claim 36 wherein said antibody is unlabeled and said kit further comprises a labeled derivative of a specific binding partner of said antibody.

39. A composition of matter comprising a complex of:
(a) a monoclonal antibody that binds HTLV-III gene product, said antibody being selected from the group of antibodies secreted from hybrid continuous cell lines having ATCC accession numbers HB9101, HB9100, and HB9102, respectively, and
(b) said gene product.

40. The composition of claim 39 wherein said complex further comprises a lymphocyte.

41. A composition of matter comprising a complex of:
(a) a monoclonal antibody capable of binding to a cell-bound antigen other than an HTLV-III gene product and produced as a result of an HTLV-III infection, said antibody being selected from the group of antibodies secreted from hybrid continuous cell lines having ATCC accession numbers HB9101, HB9100, and HB9102, respectively,
(b) said antigen.

42. A monoclonal antibody having the identifying characteristics of binding to HTLV-III antigens of 23, 41, 55, 49, and 52 kilodaltons, respectively, said antigens being capable of binding to one of the antibodies secreted by a cell line having ATCC accession numbers HB9100, HB9101, HB9102, HB9114, or HB9115.

43. A monoclonal antibody having the identifying characteristics of binding to HTLV-III antigens of 24, 28, 55, 65, and 49 kilodaltons, respectively, said antigens being capable of binding to one of the antibodies secreted by a cell line having ATCC accession number HB9100, HB9101, HB9102, HB9114, or HB9115.

44. A monoclonal antibody having the identifying characteristics of binding to HTLV-III antigens of 24; 41; and 55 kilodaltons, respectively, said antigens being capable of binding to one of the antibodies secreted by a cell line having ATCC accession number HB9100, HB9101, HB9102, HB9114, or HB9115.

45. A monoclonal antibody having the identifying characteristic of binding to HTLV-III antigens of 24, 39 and 65 kilodaltons, respectively, said antigens being capable of binding to one of the antibodies secreted by a cell line having ATCC accession number HB9100, HB9101, HB9102, HB9114, or HB9115.

46. A monoclonal antibody having the identifying characteristics of binding to an HTLV-III antigen of 55 kilodaltons, said antigen being capable of binding to one of the antibodies secreted by a cell line having ATCC accession numbers HB9100, HB9101, HB9102, HB9114, or HB9115.

* * * * *